United States Patent
Hirota et al.

(10) Patent No.: US 10,276,998 B2
(45) Date of Patent: Apr. 30, 2019

(54) SOLID-STATE LASER DEVICE AND PHOTOACOUSTIC MEASUREMENT DEVICE

(71) Applicant: FUJIFILM Corporation, Tokyo (JP)

(72) Inventors: Kazuhiro Hirota, Ashigarakami-gun (JP); Hiroyasu Ishii, Ashigarakami-gun (JP); Takuji Tada, Ashigarakami-gun (JP)

(73) Assignee: FUJIFILM Corporation, Tokyo (JP)

( * ) Notice: Subject to any disclaimer, the term of this patent is extended or adjusted under 35 U.S.C. 154(b) by 496 days.

(21) Appl. No.: 15/266,709

(22) Filed: Sep. 15, 2016

(65) Prior Publication Data

US 2017/0229830 A1    Aug. 10, 2017

Related U.S. Application Data

(63) Continuation of application No. PCT/JP2015/053476, filed on Feb. 9, 2015.

(30) Foreign Application Priority Data

Mar. 28, 2014  (JP) .................. 2014-068538

(51) Int. Cl.
*H01S 3/02*  (2006.01)
*A61B 5/00*  (2006.01)
(Continued)

(52) U.S. Cl.
CPC ............ *H01S 3/025* (2013.01); *A61B 5/0095* (2013.01); *H01S 3/061* (2013.01); *H01S 3/093* (2013.01); *H01S 3/0931* (2013.01); *H01S 3/0407* (2013.01)

(58) Field of Classification Search
CPC .......... H01S 3/025; H01S 3/061; H01S 3/093; H01S 3/0931; H01S 3/0407; A61B 5/0095
See application file for complete search history.

(56) References Cited

U.S. PATENT DOCUMENTS 3,493,888 A    2/1970  Jackson
4,232,276 A *  11/1980 Iwata ...................... H01S 3/025
                                                372/107

(Continued)

FOREIGN PATENT DOCUMENTS

JP   6-260701 A   9/1994

OTHER PUBLICATIONS

Extended European Search Report dated in European Application No. 15770301.8 on Mar. 28, 2017.

*Primary Examiner* — Armando Rodriguez
(74) *Attorney, Agent, or Firm* — Birch, Stewart, Kolasch & Birch, LLP

(57) ABSTRACT

In a solid-state laser device and a photoacoustic measurement device including the solid-state laser device, the distance between a laser rod and a flash lamp is narrowed. A shielding lid shields mirrors and an optical path of laser light from the outside. A first portion of a frame body of a laser chamber is exposed from the shielding lid. A flash lamp stored in the frame body of the laser chamber is able to be removed from and inserted into the first portion of the frame body. A thin film portion having a thickness smaller than the thickness of other portions of the shielding lid is provided in at least a part of a region of the shielding lid covering the optical path of a light beam on the outside in a longitudinal direction from the first portion of the frame body of the laser chamber.

20 Claims, 6 Drawing Sheets

(51) Int. Cl.
*H01S 3/093* (2006.01)
*H01S 3/06* (2006.01)
*H01S 3/04* (2006.01)

(56) References Cited

U.S. PATENT DOCUMENTS

| | | | |
|---|---|---|---|
| 4,653,063 A | 3/1987 | Acharekar et al. | |
| 2016/0099544 A1* | 4/2016 | Hoshino | H01S 5/183 356/432 |
| 2016/0226214 A1* | 8/2016 | Ishii | A61B 5/0095 |

* cited by examiner

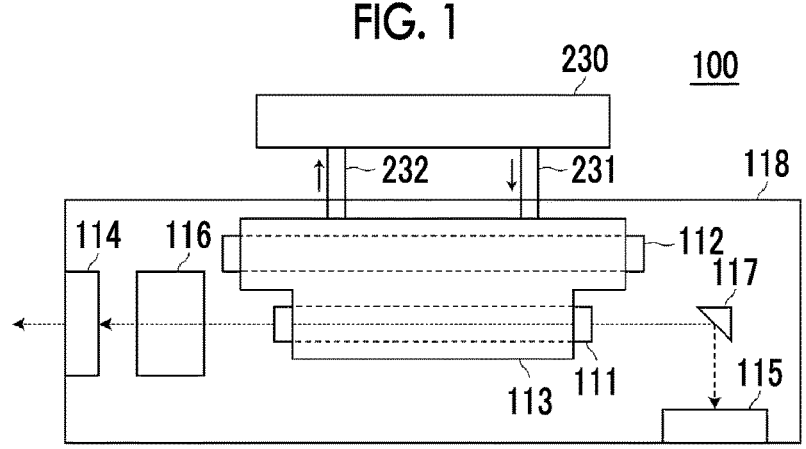
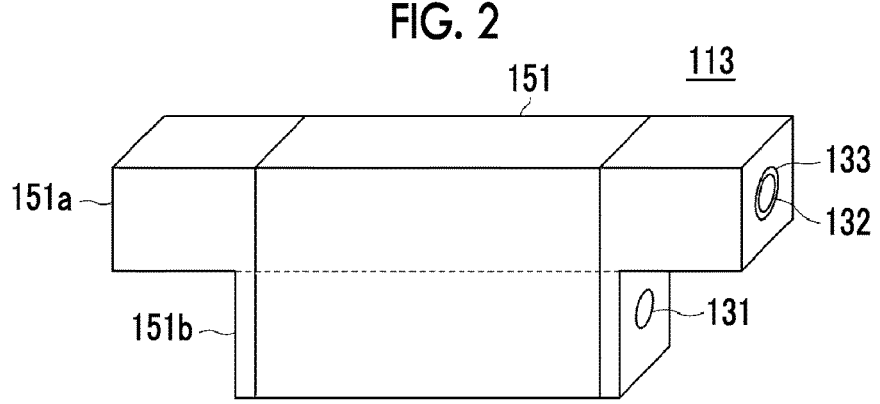
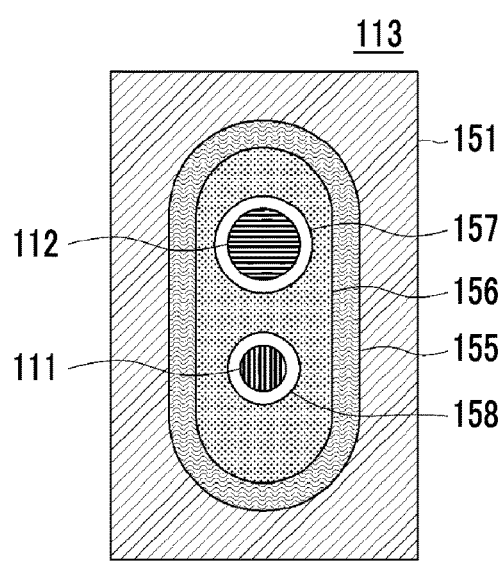

SOLID-STATE LASER DEVICE AND PHOTOACOUSTIC MEASUREMENT DEVICE

CROSS-REFERENCE TO RELATED APPLICATIONS

This application is a Continuation of PCT International Application No. PCT/JP2015/053476 filed on Feb. 9, 2015, which claims priority under 35 U.S.C. § 119(a) to Japanese Patent Application No. 2014-068538 filed on Mar. 28, 2014. Each of the above application(s) is hereby expressly incorporated by reference, in its entirety, into the present application.

BACKGROUND OF THE INVENTION

1. Field of the Invention

The present invention relates to a solid-state laser device, and in particular, to a solid-state laser device having a laser chamber storing a laser rod and an excitation lamp.

The present invention also relates to a photoacoustic measurement device including the solid-state laser device.

2. Description of the Related Art

Hitherto, as one kind of image inspection method which can noninvasively inspect a state inside a living body, an ultrasonography method has been known. In ultrasonography, an ultrasound probe which can transmit and receive an ultrasonic wave is used. If an ultrasonic wave is transmitted from the ultrasound probe to a subject (living body), the ultrasonic wave advances through the inside of the living body, and is reflected from a tissue interface. The reflected ultrasonic wave is received by the ultrasound probe, and a distance is calculated based on the time until the reflected ultrasonic wave returns to the ultrasound probe, whereby it is possible to image the status of the inside.

Furthermore, photoacoustic imaging which images the inside of a living body using a photoacoustic effect is known. In general, in photoacoustic imaging, the inside of the living body is irradiated with pulse laser light. Inside the living body, a living body tissue absorbs energy of pulse laser light, and an ultrasonic wave (photoacoustic wave) is generated due to adiabatic expansion caused by energy. The photoacoustic wave is detected by an ultrasound probe or the like, and a photoacoustic image is constituted based on a detection signal, whereby it is possible to visualize the inside of the living body based on the photoacoustic wave.

In a measurement of a photoacoustic wave, in many cases, it is necessary to emit pulse laser light with high intensity, and a flash lamp excited solid-state laser device is widely used for a light source. The solid-state laser device has a laser rod (laser medium), and a flash lamp (excitation lamp) which excites the laser rod. The laser rod and the excitation lamp are stored inside a laser chamber. The inside of the laser chamber is provided with a reflection surface which allows efficient irradiation of the laser rod with light emitted from the flash lamp or a diffuser which diffuses light and uniformly transmits light to the laser rod.

In the solid-state laser device, if dust or dirt sticks to an end surface of the laser rod or a reflection surface of a resonator mirror, the energy of laser light is concentrated on this portion, the rod end surface or the mirror reflection surface may be damaged. In order to protect the laser rod or the resonator mirror from dust or dirt, a structure in which a laser rod or a resonator mirror is stored in a boxlike base and the top of the base is covered with a lid to seal the inside of the base airtight is considered (for example, see JP1994-260701A (JP-H06-260701A)).

SUMMARY OF THE INVENTION

The flash lamp is a consumable, and needs to be replaced regularly. In order to facilitate the replacement of the flash lamp, it is considered that a flash lamp portion of the laser chamber is exposed from a lid portion, and the flash lamp is pulled out from the laser chamber without opening the lid portion. In this case, it is preferable that the end portion of the laser chamber is sealed with the lid portion such that the sealed state of the inside is maintained even at the time of replacement.

In a case where the flash lamp portion of the laser chamber is exposed from the lid portion, if the end portion of the laser chamber is sealed with the lid portion, the extension direction of the flash lamp and the extension direction of the laser rod are divided by the lid portion. In order to avoid interference of the lid portion with the flash lamp or interference of the lid portion with the laser rod or light emitted from the laser rod, it is necessary to provide that there is a distance between the flash lamp and the laser rod.

In general, when there is a short distance between the flash lamp and the laser rod, the excitation efficiency is increased. In order to avoid interference of the lid portion, if the distance between the flash lamp and the laser rod is increased, the excitation efficiency is decreased by an increase in distance. In particular, in many cases, a hole portion, into which the flash lamp of the laser chamber is inserted, has an O ring attachment portion for end portion sealing, and the O ring attachment portion has a size greater than the diameter of the hole portion into which the flash lamp is inserted. In order to avoid interference of the O ring attachment portion with the lid portion, it is not possible to narrow the distance between the flash lamp and the laser rod, making it difficult to improve the excitation efficiency.

In consideration of the above, an object of the invention is to provide a solid-state laser device capable of narrowing the distance between a laser rod center and a flash lamp center while facilitating replacement of an excitation lamp.

Another object of the invention is to provide a photoacoustic measurement device including the solid-state laser device described above.

In order to attain the above-described object, the invention provides a solid-state laser device comprising a laser rod, an excitation lamp which emits excitation light to the laser rod, a laser chamber which includes a frame body having an internal space storing the laser rod and the excitation lamp and transmits light emitted from the excitation lamp to the laser rod inside the frame body, a first portion of the frame body storing the excitation lamp having a first hole portion having a diameter greater than the outer diameter of the excitation lamp and a second portion of the frame body storing the laser rod having a second hole portion into which the laser rod is inserted, a pair of mirrors provided on the optical path of a light beam emitted from the laser rod, a housing to which the laser chamber and the pair of mirrors are attached, and a shielding portion which shields the second portion of the frame body of the laser chamber attached to the housing, the pair of mirrors, and the optical path of the light beam emitted from the laser rod from the outside. The first portion of the frame body of the laser chamber further has an O ring attachment portion in which an O ring having an outer diameter greater than the diameter of the first hole portion is attached to an end portion in a longitudinal direction, the excitation lamp is able to be removed from and inserted into the laser chamber intermediated by the first hole portion, and the thickness of at least a part of a region of the shielding portion covering the optical path of the light beam emitted from the second hole portion is smaller than the thickness of other portions of the shielding portion on the outside in the longitudinal direction from the first portion of the frame body of the laser chamber.

In the solid-state laser device of the invention, the shielding portion may include a plate-shaped lid portion which has an opening which is wider than the laser chamber and an insulating member which closes the opening of the plate-shaped lid portion and has a duct, through which the light beam emitted from the laser rod passes, and the laser chamber may be attached to the housing intermediated by the insulating member.

The first portion of the frame body of the laser chamber may be exposed from the insulating member.

The duct may be a through hole formed in the insulating member, and the thickness of a partition wall of the insulating member which separates the outside on the first portion side of the frame body from the through hole may be smaller than the thickness of the plate-shaped lid portion.

The duct may have a cylindrical shape, the diameter of the cylindrical duct may be greater than the diameter of the light beam emitted from the laser rod, and the central axis of the light beam passing through the cylindrical duct may be deviated in the direction of the first portion of the frame body of the laser chamber from the central axis of the cylindrical duct.

The duct may be a groove which is formed in the insulating member and has an opening in the direction of the first portion of the frame body of the laser chamber. In this case, the shielding portion may further have a film which covers the opening of the duct, and the thickness of the film may be smaller than the thickness of the plate-shaped lid portion.

The shielding portion may be constituted of a plate-shaped lid portion, and of the plate-shaped lid portion, the thickness of at least a part of a region covering the optical path of the light beam emitted from the second hole portion may be smaller than the thickness of other portions of the plate-shaped lid portion on the outside in the longitudinal direction from the first portion of the frame body of the laser chamber.

The frame body may be formed of a metal material.

The solid-state laser device of the invention may further include an insulating block which is detachably attached to the first portion of the frame body of the laser chamber intermediated by an O ring.

The length in the longitudinal direction of the first portion of the frame body may be longer than the length in the longitudinal direction of the second portion of the frame body.

The laser chamber may further have, in the space, a glass material which has a first storage hole having an inner diameter greater than the outer diameter of the excitation lamp and storing the excitation lamp, and a second storage hole having an inner diameter greater than the outer diameter of the laser rod and storing the laser rod therein.

The invention also provides a photoacoustic measurement device comprising the solid-state laser device of the invention, a photoacoustic wave detection section for detecting a photoacoustic wave generated in a subject after the subject has been irradiated with laser light emitted from the solid-state laser device, and a signal processing section for carrying out signal processing based on the detected photoacoustic wave.

According to the solid-state laser device and the photoacoustic measurement device of the invention, it is possible to narrow the distance between a laser rod center and a flash lamp center to increase excitation efficiency while facilitating replacement of an excitation lamp.

BRIEF DESCRIPTION OF THE DRAWINGS

FIG. 1 is a block diagram showing a solid-state laser device according to a first embodiment of the invention.

FIG. 2 is a perspective view showing the appearance of a laser chamber.

FIG. 3 is a sectional view showing a section of a central portion of the laser chamber.

DESCRIPTION OF THE PREFERRED EMBODIMENTS

Figure 4:
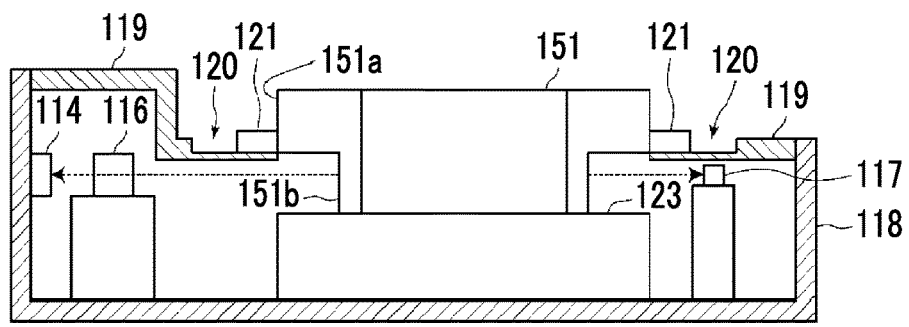
FIG. 4 is a sectional view showing a section of the vicinity of the center of the solid-state laser device.

Hereinafter, an embodiment of the invention will be described in detail referring to the drawings. FIG. 1 shows a solid-state laser device according to a first embodiment of the invention. A solid-state laser device 100 has a laser rod 111, a flash lamp 112, a laser chamber 113, mirrors 114 and 115, a Q switch 116, and a prism 117. The laser rod 111, the flash lamp 112, the laser chamber 113, the mirrors 114 and 115, the Q switch 116, and the prism 117 are disposed in a boxlike housing 118. Though not shown in FIG. 1, the solid-state laser device 100 has a plate-shaped shielding lid which shields the internal space of the housing 118 from the outside. FIG. 1 is a diagram illustrating the components of the solid-state laser device 100, and the spatial positional relationship among the components in FIG. 1 is not necessarily accurately drawn.

The laser rod 111 is a laser medium. For the laser rod 111, for example, alexandrite crystal formed in a rod shape is used. A laser medium which is used for the laser rod 111 is not particularly limited, and YAG crystal, such as neodymium YAG (yttrium-aluminum-garnet (Nd:YAG)), may be used.

The flash lamp 112 is an excitation lamp, and emits excitation light to excite the laser rod 111. The laser rod 111 and the flash lamp 112 are stored in the laser chamber 113. The laser chamber 113 has a space for storing the laser rod 111 and the flash lamp 112 therein, and transmits light emitted from the excitation lamp to the laser rod 111 therein. For example, a reflection surface is formed on the inside of the laser chamber 113, and the laser rod 111 is irradiated directly with light emitted from the flash lamp 112, or the laser rod 111 is irradiated with light emitted from the flash lamp 112 and reflected by the reflection surface.

The laser chamber 113 is connected to cooling equipment 230 through pipings 231 and 232. The cooling equipment 230 is equipment for cooling the laser rod 111 and the flash lamp 112. For example, the cooling equipment 230 feeds a cooling medium, such as pure water, into the laser chamber 113 through the piping 231. The cooling equipment 230 receives water from the laser chamber 113 through the piping 232, decreases the temperature of the cooling medium, and then, feeds the cooling medium into the laser chamber 113 again. In this way, the cooling medium is circulated, whereby it is possible to maintain the temperature of the laser rod 111 in the laser chamber 113 in a desired temperature range.

The mirrors 114 and 115 are opposed to each other with the laser rod 111 sandwiched therebetween, and a resonator is constituted of the mirrors 114 and 115. For example, the mirror 114 is attached to the side surface of the housing 118 in a transverse direction, and the mirror 115 is attached to the side surface of the housing 118 in a longitudinal direction orthogonal to the side surface in the transverse direction. A prism 117 is disposed between the laser rod 111 and the mirror 115, and light emitted from the laser rod 111 is turned by the prism 117 and is directed toward the mirror 115. The prism 117 may not be provided, and the optical path in the optical resonator may be made linear. The mirror 114 is an output coupler (OC), and the mirror 115 is a total reflection mirror. Laser light as output light is emitted from the mirror 114.

The Q switch 116 is inserted into the resonator. In FIG. 1, the Q switch 116 is disposed on the optical axis of light induced and emitted from the laser rod 111 between the laser rod 111 and the mirror 114. For the Q switch 116, for example, a Pockels cell which changes the polarization state of light transmitted therethrough according to an applied voltage is used. The Q switch 116 changes the Q value of the resonator according to the applied voltage. After the excitation of the laser rod 111, the Q switch 116 is controlled to rapidly switch the Q value of the resonator from a low Q state to a high Q state, whereby it is possible to make a laser perform Q switch pulse oscillation. In addition to the Pockels cell, a quarter wave plate or a polarizer may be disposed on the optical path of the resonator.

FIG. 2 is a perspective view showing the appearance of the laser chamber 113. In FIG. 2, holes and the like for connecting the pipings 231 and 232 (see FIG. 1) are not shown. The laser chamber 113 has a frame body 151. The frame body 151 is formed of, for example, a metal material. The frame body 151 has an internal space storing the laser rod 111 and the flash lamp 112. The laser chamber 113 has a diffuser which diffuses light emitted from the flash lamp 112 and transmits light to the laser rod 111 inside the frame body 151. Alternatively, the laser chamber 113 may have a reflection surface instead of the diffuser, and may have such a structure as to reflect light of the flash lamp and to transmit light to the laser rod.

The frame body 151 has a first portion 151a which stores the flash lamp 112, and a second portion 151b which stores the laser rod 111. The first portion 151a of the frame body has a first hole portion 132 having a diameter greater than the outer diameter of the flash lamp 112. The first portion 151a of the frame body has an O ring attachment portion 133, to which an O ring is attached, in the end portion in the longitudinal direction. The outer diameter of the O ring and the outer diameter of the O ring attachment portion 133 are greater than the diameter of the first hole portion 132. For example, when the diameter of the flash lamp 112 is 5 mm, the diameter of the first hole portion 132 is 6 mm, and the outer diameters of the O ring and the O ring attachment portion 133 are 7 mm. The second portion 151b of the frame body has a second hole portion 131 into which the laser rod 111 is inserted.

The flash lamp 112 can be removed from and inserted into the laser chamber 113 in the longitudinal direction through the first hole portion 132. The length of the first portion 151a of the frame body in the longitudinal direction is longer than the length of the second portion 151b of the frame body in the longitudinal direction. The lengths of the first portion 151a and the second portion 151b of the frame body in the longitudinal direction may be equal.

FIG. 3 shows a section of a central portion of the laser chamber 113. The laser chamber 113 has a diffusion material 155 and a glass material 156 in the internal space of the frame body 151. The diffusion material 155 surrounds the laser rod 111 and the flash lamp 112 through the glass material 156. The diffusion material 155 diffuses and reflects incident light. The diffusion material 155 constitutes a reflection surface which reflects light emitted from the flash lamp 112. For the diffusion material 155, for example, barium sulfate, magnesium oxide, or the like is available. Alternatively, alumina ceramics, Spectralon (the product name of Labsphere Inc. in U.S.), or the like may be used.

The glass material 156 has a first storage hole 157 which stores the flash lamp 112 therein, and a second storage hole 158 which stores the laser rod 111 therein. The inner diameter of the first storage hole 157 is greater than the outer diameter of the flash lamp 112. The inner diameter of the second storage hole 158 is greater than the outer diameter of the laser rod 111. A space between the first storage hole 157 an the flash lamp 112 is filled with a cooling medium, and a space between the second storage hole 158 and the laser rod 111 is filled with a cooling medium. The diameter of the flash lamp 112 is, for example, about 5 mm. The distance between the center of the laser rod 111 and the center of the flash lamp 112 is, for example, about 6 mm to 7 mm.

FIG. 4 shows a section of the vicinity of the center of the solid-state laser device. The mirror 114, the Q switch 116, the prism 117, and the like are attached to the housing 118. The frame body 151 of the laser chamber is attached to the housing 118 through an insulating member 123. A shielding lid (shielding portion) 119 covers the housing 118, and shields the optical path of a light beam emitted from the mirror 114, the Q switch 116, the prism 117, or the laser rod 111 from the outside. The shielding lid 119 is, for example, insulating resin, such as polycarbonate, nylon, or ABS resin.

Of the frame body 151 of the laser chamber, the first portion 151a is exposed from the shielding lid 119. To the first portion 151a of the frame body exposed to the outside, an insulating block 121 for insulating the electrodes of the flash lamp 112 (see FIG. 1) is attached through an O ring. The shielding lid 119 has a thin film portion 120 having a thickness smaller than the thickness of other portions of shielding lid 119 in at least a part of a region covering the optical path of laser light on the outside in the longitudinal direction from the first portion 151a of the frame body.

Figure 5:
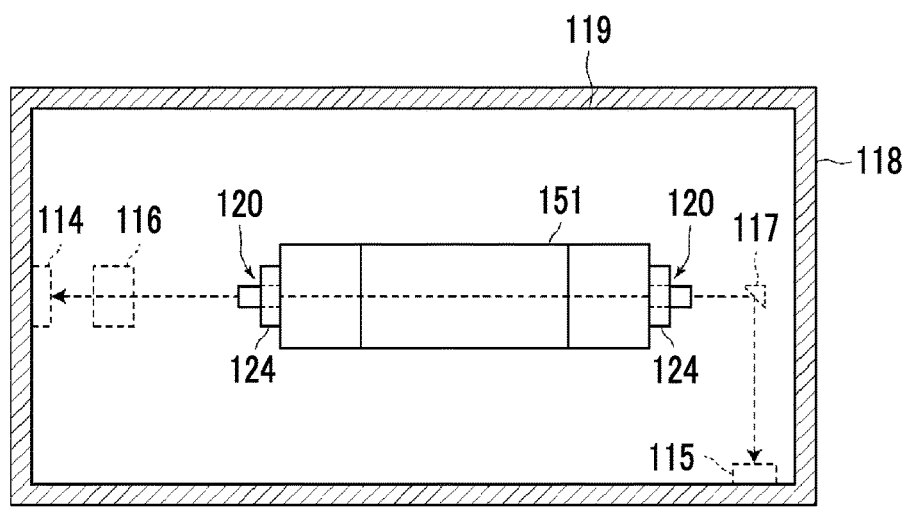
FIG. 5 is a top view of the solid-state laser device.

FIG. 5 is a top view of the solid-state laser device. The mirrors 114 and 115, the Q switch 116, and the prism 117 are sealed in the housing 118 by the shielding lid 119. The first portion 151a of the frame body of the laser chamber is exposed from the shielding lid 119, and the insulating block 121 is on the top of the shielding lid 119. The insulating block 121 is formed of, for example, resin, such as ABS resin or polyacetal resin (POM). The insulating block 121 is screwed to the frame body 151 through the O ring in a state where the solid-state laser device is used. The insulating block 121 is detached from the frame body 151 when replacing the flash lamp 112. The shielding lid 119 has the thin film portion 120 in a predetermined range centering on the optical axis of laser light from the end portion of the first portion 151a of the frame body in the longitudinal direction of the frame body 151.

Figure 6:
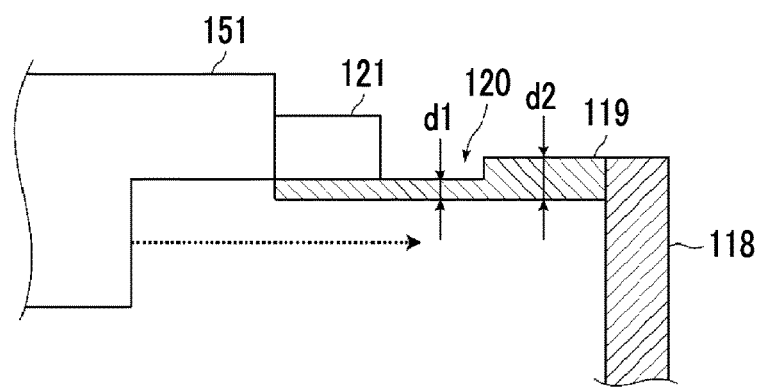
FIG. 6 is a sectional view showing the vicinity of an insulating block of FIG. 4 on an enlarged scale.

FIG. 6 shows the vicinity of the insulating block 121 on an enlarged scale. The shielding lid 119 extends to the boundary between the frame body 151 and the insulating block 121 so as to maintain sealing of the inside even when the insulating block 121 is detached from the frame body 151. The insulating block 121 is attached to the frame body 151 on the shielding lid 119. Of the shielding lid 119, a portion positioned below the insulating block 121 is the thin film portion 120.

The thickness of the thin film portion 120 of the shielding lid 119 is referred to as d1, and the thickness of other portions is referred to as d2. For example, the thickness d1 of the thin film portion 120 of the shielding lid 119 is 0.5 mm, and the thickness d2 of other portions is 6 mm. If the thickness of a portion of the shielding lid 119 in contact with the end portion of the first portion 151a of the frame body is not the thickness (d1) of the thin film portion 120 but is the normal thickness (d2), it is necessary to move the positions of the insulating block 121 and the first hole portion 132 and the O ring attachment portion 133 (see FIG. 2) in the first portion 151a of the frame body by the difference in thickness from the thin film portion 120 in a direction away from the second hole portion 131. If the insulating block 121 and the first hole portion 132 of the frame body 151 remain as they are, the thickness of the thin film portion 120 becomes the normal thickness d2, the shielding lid 119 may interfere with laser light.

In a case where the first portion 151a of the frame body is exposed from the shielding lid 119, in particular, the O ring attachment portion 133 in the end portion is likely to interfere with the shielding lid 119. In this embodiment, of the shielding lid 119, a predetermined range from the end portion of the first portion 151a of the frame body having the O ring attachment portion 133 is the thin film portion 120. With this, it is possible to reduce the distance between the laser rod 111 and flash lamp 112 while allowing replacement of the flash lamp 112 without exposing an optical member inside the resonator, compared to a case where the shielding lid 119 is formed to have a uniform thickness, and to improve excitation efficiency.

If the thickness of the entire shielding lid 119 is made small, it is possible to narrow the distance between the laser rod 111 and the flash lamp 112. However, if the entire shielding lid 119 is formed to have the same thickness as the thin film portion 120, the strength of the shielding lid 119 is insufficient. In this embodiment, in particular, of the shielding lid 119, the thickness of a part of a region extending from the first portion 151a of the frame body and covering the optical path of laser light is made small; thus, it is possible to narrow the distance between the laser rod 111 and the flash lamp 112 while maintaining the overall strength.

Figure 7:
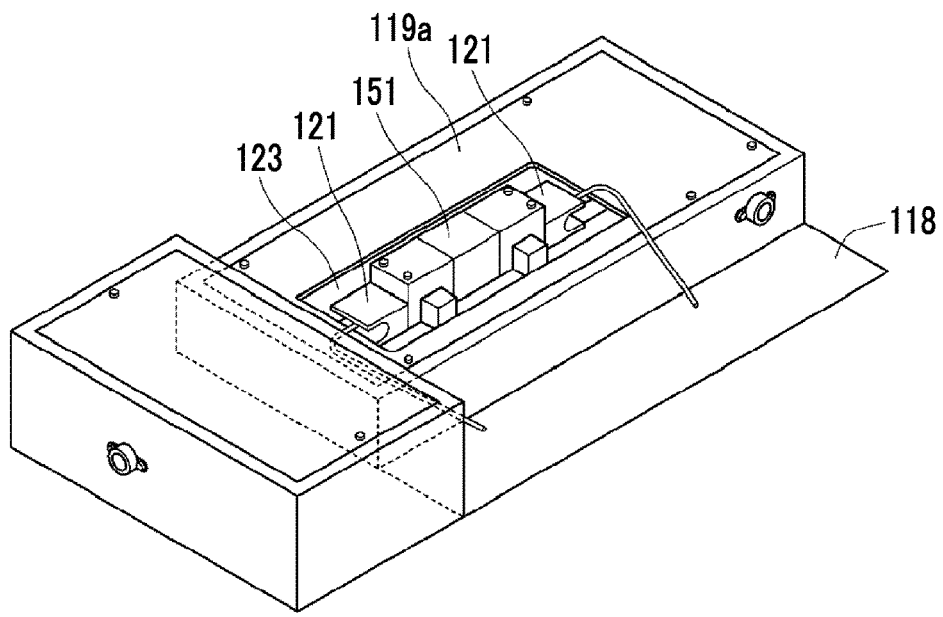
FIG. 7 is a perspective view showing a solid-state laser device according to a second embodiment of the invention.
Figure 8:
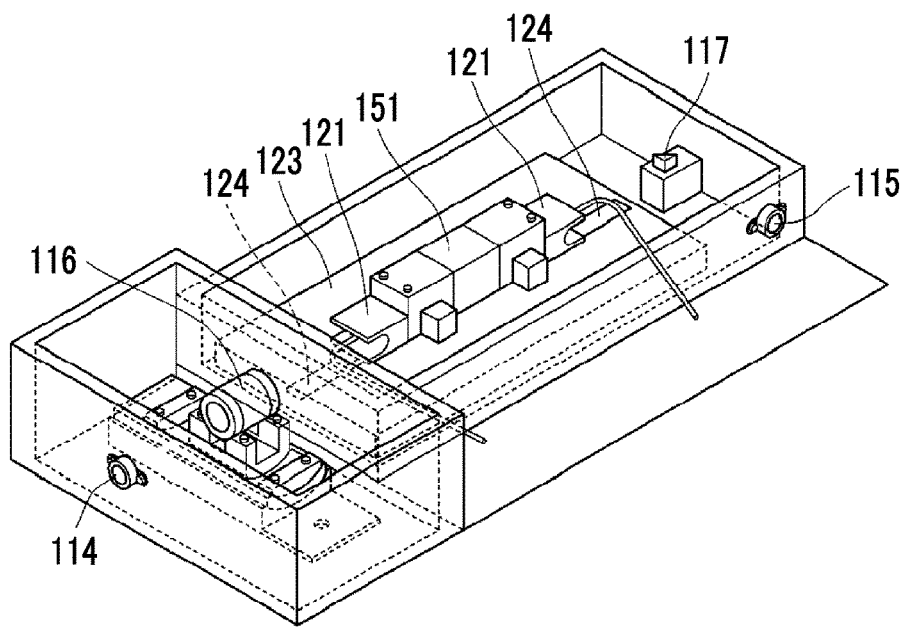
FIG. 8 is a perspective view showing the solid-state laser device in a state where a shielding lid is detached from FIG. 7.

Next, a second embodiment of the invention will be described. FIG. 7 is a perspective view showing a solid-state laser device according to the second embodiment of the invention. FIG. 8 shows the solid-state laser device in a state where a shielding lid 119a is detached from FIG. 7. Mirrors 114 and 115, a Q switch 116, and a prism 117 are sealed in a housing 118 by a plate-shaped shielding lid 119a. The shielding lid 119a is, formed of, metal, such as aluminum or stainless steel.

At the time of light emission of the flash lamp 112, since a high voltage of several kV is applied to the laser chamber 113, in a case where a metal plate is used for the shielding lid, it is necessary to isolate the shielding lid 119a from the laser chamber 113 in order to prevent the high voltage from being applied to the shielding lid 119a. In this embodiment, the shielding lid 119a has an opening wider than a region corresponding to the laser chamber 113 (the first portion 151a of the frame body). The opening of the shielding lid 119a is closed with the laser chamber 113 and the insulating member 123. The first portion 151a of the frame body of the laser chamber 113 is exposed from the insulating member 123.

Figure 9:
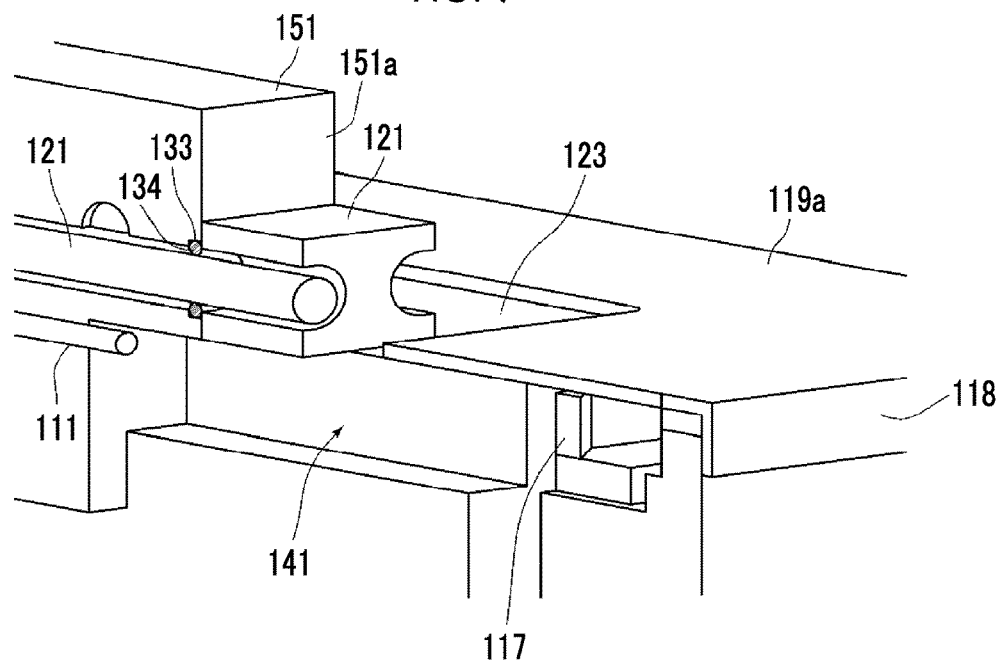
FIG. 9 is a sectional perspective view showing a section of the vicinity of an end portion of a first portion of a frame body of a laser chamber on an enlarged scale.
Figure 10:
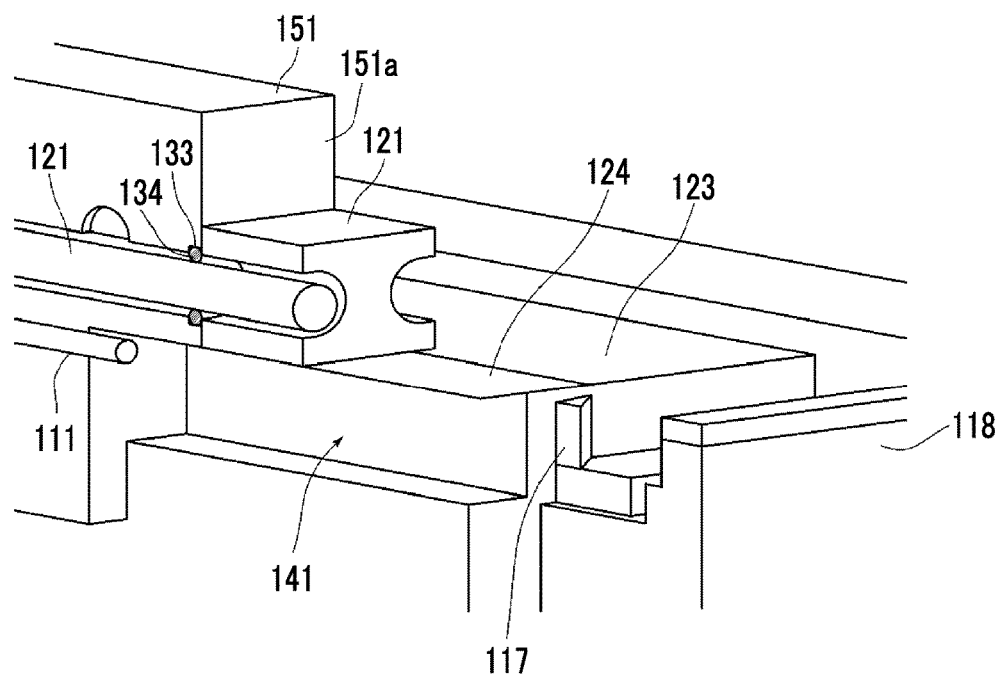
FIG. 10 is a sectional perspective view showing a state where a shielding lid is removed from FIG. 9.

FIG. 9 is a sectional perspective view showing a section of the vicinity of the end portion of the first portion 151a of the frame body of the laser chamber on an enlarged scale. FIG. 10 shows a state where the shielding lid 119a is removed from FIG. 9. The frame body 151 has an O ring attachment portion 133 in the end portion in the longitudinal direction (also see FIG. 2). An O ring 134 is held to be sandwiched between the O ring attachment portion 133 and the insulating block 121. The O ring 134 seals the gap between the first storage hole 157 (see FIG. 3) of the frame body 151 and the flash lamp 112, and prevents overflow of a cooling medium for cooling the flash lamp 112 from the frame body 151 to the outside.

In a case where the mirror 115 is disposed in a traveling direction of light emitted from the laser rod 111, since the mirror 115 has a size greater than the prism 117, it is necessary to increase the height of the shielding lid 119a by that amount. If the height of the shielding lid 119a in a direction of removing the flash lamp 112 is increased, the flash lamp 112 hits the elevated portion of the shielding lid 119a at the time of removing the flash lamp 112, making it difficult to remove the flash lamp 112. In this embodiment, light is bent at 90° using the prism 117 having a size greater than the mirror 115, and the mirror 115 is disposed on the side surface in the longitudinal direction of the housing, making it easy to remove the flash lamp 112.

The insulating member 123 has a groove 141 having an opening on the first portion 151a side of the frame body of the laser chamber. The groove 141 is formed in, for example, a rectangular shape. The groove 141 constitutes a duct through which a light beam emitted from the laser rod 111 passes. As shown in FIG. 10, an opening portion of the groove (duct) 141 is covered with a thin film 124 (also see FIG. 8). The thin film 124 is, for example, a polyimide film, and the thickness thereof is smaller than the thickness of the plate-shaped shielding lid 119a. For example, the thickness (corresponding to d2 of FIG. 6) of the shielding lid 119a is 6 mm, and the thickness of the thin film 124 is 100 μm. The insulating block 121 is attached to the end portion of the first portion 151a of the frame body of the laser chamber on the thin film 124. In this embodiment, the insulating member 123 and the thin film 124 constitute a part of a shielding portion.

Figure 11:
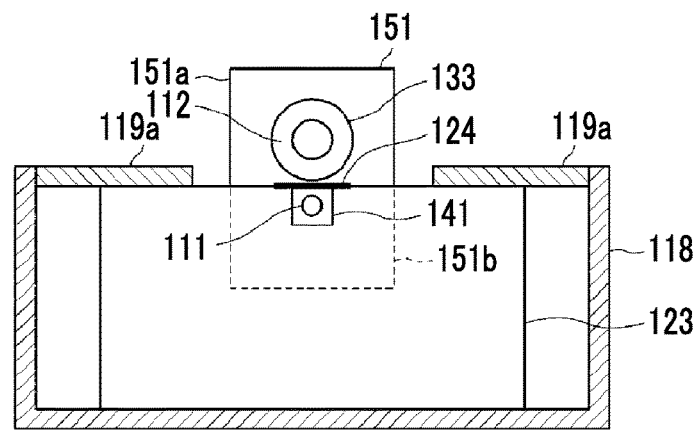
FIG. 11 is a sectional view showing a section of the vicinity of the first portion of the frame body.

FIG. 11 shows a section of the vicinity of the first portion 151a of the frame body. The inside of the housing 118 is closed with the shielding lid 119a and the insulating member 123. The frame body 151 of the laser chamber is attached to the housing 118 through the insulating member 123. The first portion 151a of the frame body is exposed from the insulating member 123, and the second portion 151b is buried in the insulating member 123. The first portion 151a of the frame body has the O ring attachment portion 133 in the attachment portion of the insulating block 121. Laser light emitted from the laser rod 111 passes through the duct 141. The top of the duct 141 is covered with the thin film 124, and the optical path of laser light is protected by the insulating member 123 and the thin film 124 from the outside.

For example, it is assumed that the diameter of the laser rod 111 is 3 mm, the diameter of the flash lamp 112 is 5 mm, and the distance between the axes of both of the laser rod 111 and the flash lamp 112 is 7 mm. In this case, the shortest distance between the laser rod 111 and the flash lamp 112 becomes 3 mm. If the wire diameter of the O ring for end surface sealing is 1 mm, the shortest distance between the O ring attachment portion 133 and the laser rod 111 becomes about 1.25 mm. Since this distance is short, if a geometric tolerance and a range of fine adjustment of an optical axis are considered, it is difficult to produce a duct (through hole) passing through the insulating member 123 only with machining. Since a high voltage is applied at the time of turning on the flash lamp 112, it is preferable that the laser chamber 113 is attached to the housing intermediated by the insulating member 123; however, the insulating member 123 has poor machining accuracy compared to a metal member. Accordingly, in this embodiment, a groove with an opened top is formed in the insulating member 123, and the top of the groove is covered with the thin film 124.

In this embodiment, the optical path (duct 141) of laser light is covered with the thin film 124, and the thickness of a partition wall which separates the duct 141 from the outside is smaller than the thickness of the shielding lid 119a. The thickness of this portion is made small, whereby, in particular, it is possible to avoid interference between the O ring attachment portion 133 and the partition wall which separates the duct 141 from the outside. Accordingly, it is possible to reduce the distance between the laser rod 111 and flash lamp 112 while allowing replacement of the flash lamp 112 without exposing an optical member inside the resonator, compared to a case where the shielding lid 119a is formed to have a uniform thickness, and to improve excitation efficiency.

Figure 12:
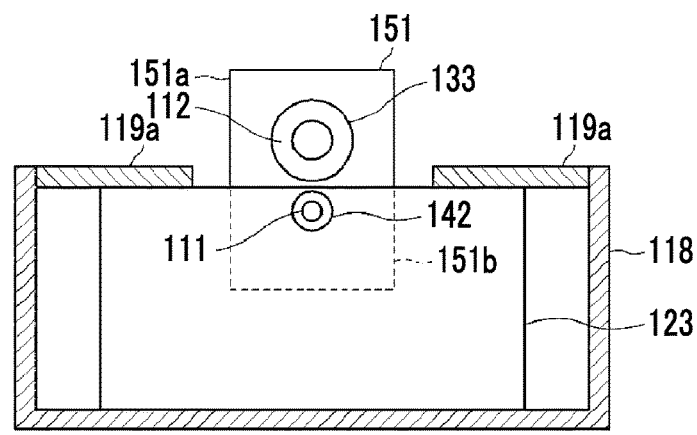
FIG. 12 is a sectional view showing a section of the vicinity of the first portion of the frame body in a first modification example.

In the above description, although an example where the thin film 124 is used as the partition wall which separates the duct 141 from the outside has been described, the invention is not limited thereto. FIG. 12 shows a section of the vicinity of the first portion 151a of the frame body of the solid-state laser device in a first modification example. In this example, a through hole 142 formed in the insulating member 123 constitutes a duct. The through hole (duct) 142 is formed in, for example, a cylindrical shape. The thickness of the partition wall (the wall portion of the duct 142) of the insulating member 123 which separates the outside on the first portion 151a side of the frame body and the duct 142 is smaller than the thickness of the shielding lid 119a. If machining accuracy is increased, even though such a duct 142 is formed, the same effects as described above are obtained.

Figure 13:
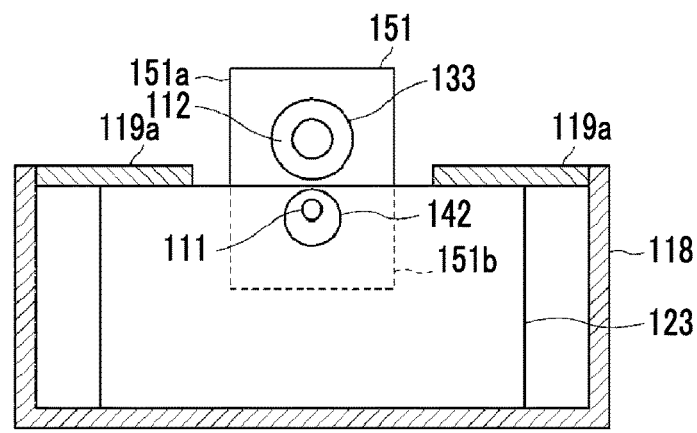
FIG. 13 is a sectional view showing a section of the vicinity of the first portion of the frame body in a second modification example.

FIG. 13 shows a section of the vicinity of the first portion 151a of the frame body of the solid-state laser device in a second modification example. In this modification example, as in the first modification example, a cylindrical through hole 142 formed in the insulating member 123 constitutes a duct. In the second modification example, the diameter of the through hole (duct) 142 is sufficiently greater than the diameter of the light beam emitted from the laser rod 111, and the central axis of the light beam passing through the duct 142 is deviated in the direction of the first portion 151a of the frame body of the laser chamber from the central axis of the cylindrical duct 142. The deviation between the central axis of the duct 142 and the central axis is set to at least 1 mm, for example, about 2 mm. In this way, the central axis of the duct 142 is deviated from the central axis of laser light, whereby it is possible to provide a margin to optical path adjustment compared to a case where both central axes match each other.

Figure 14:
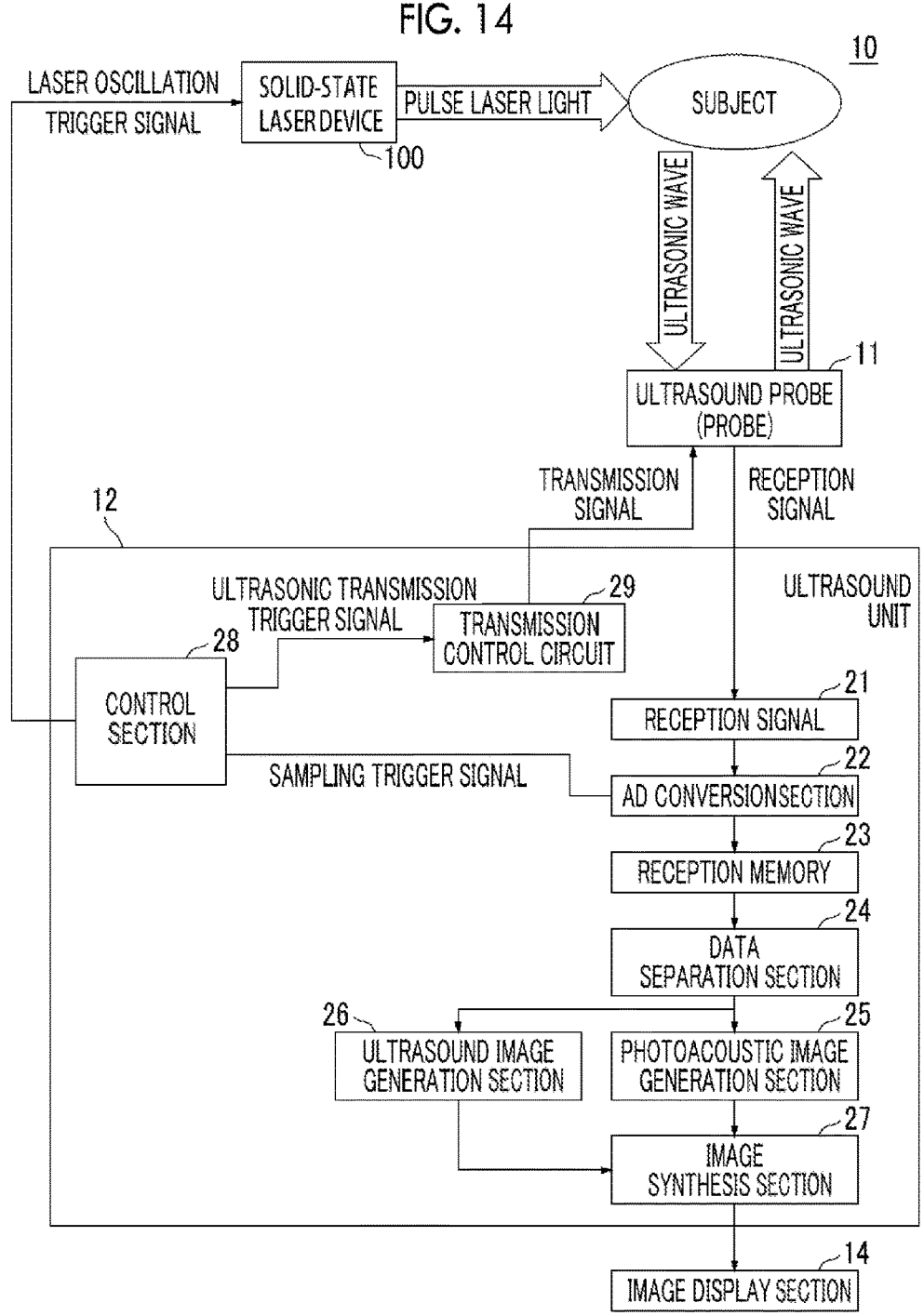
FIG. 14 is a block diagram showing a photoacoustic measurement device including the solid-state laser device.

Subsequently, a photoacoustic measurement device including the solid-state laser device of the invention will be described. FIG. 14 shows a photoacoustic measurement device including the solid-state laser device 100. The photoacoustic measurement device 10 comprises an ultrasound probe (probe) 11, an ultrasound unit 12, and the solid-state laser device 100. In the embodiment of the invention, although an ultrasonic wave is used as an acoustic wave, the invention is not limited to the ultrasonic wave, and an acoustic wave having an audio frequency may be used as long as an appropriate frequency has to be selected according to an inspection target, the measurement conditions, or the like.

Laser light emitted from the solid-state laser device 100 is guided to the probe 11, for example, using light guide means, such as an optical fiber, and is irradiated from the probe 11 toward a subject. The irradiation position of laser light is not particularly limited, and the irradiation of laser light may be performed from a place other than the probe 11.

Inside the subject, an optical absorber absorbs energy of irradiated laser light, and thus, an ultrasonic wave (acoustic wave) is generated. The probe 11 is an acoustic wave detection section, and has, for example, a plurality of ultrasonic transducers arranged in a one-dimensional manner. The probe 11 detects an acoustic wave (photoacoustic wave) from the inside of the subject by a plurality of ultrasonic transducers arranged in a one-dimensional manner. The probe 11 transmits an acoustic wave (ultrasonic wave) to the subject and receives a reflected acoustic wave (reflected ultrasonic wave) of the transmitted ultrasonic wave from the inside of the subject.

The ultrasound unit 12 is a signal processing section. The ultrasound unit 12 has a reception circuit 21, an AD conversion section 22, a reception memory 23, a data separation section 24, a photoacoustic image generation section 25, an ultrasound image generation section 26, an image synthesis section 27, a control section 28, and a transmission control circuit 29.

The reception circuit 21 receives a detection signal of the photoacoustic wave detected by the probe 11. Furthermore, the reception circuit 21 receives a detection signal of the reflected ultrasonic wave detected by the probe 11. The AD conversion section 22 converts the detection signals of the photoacoustic wave and the reflected ultrasonic wave received by the reception circuit 21 to digital signals. The AD conversion section 22 samples the detection signals of the photoacoustic wave and the reflected ultrasonic wave based on, for example, a sampling clock signal having a predetermined period. The AD conversion section 22 stores the sampled detection signals (sampling data) of the photoacoustic wave and the reflected ultrasonic wave in the reception memory 23.

The data separation section 24 separates sampling data of the detection signal of the photoacoustic wave stored in the reception memory 23 from sampling data of the detection signal of the reflected ultrasonic wave. The data separation section 24 inputs sampling data of the detection signal of the photoacoustic wave to the photoacoustic image generation section 25. Furthermore, the data separation section 24 inputs the separated sampling data of the reflected ultrasonic wave to the ultrasound image generation section (a reflected acoustic image generation section) 26.

The photoacoustic image generation section 25 generates a photoacoustic image based on the detection signal of the photoacoustic wave detected by the probe 11. The generation of the photoacoustic image includes, for example, image reconstruction, such as phase matching addition, detection, logarithmic conversion, and the like. The ultrasound image generation section 26 generates an ultrasound image (reflected acoustic image) based on the detection signal of the reflected ultrasonic wave detected by the probe 11. The generation of the ultrasound image includes image reconstruction, such as phase matching addition, detection, logarithmic conversion, and the like.

The image synthesis section 27 synthesizes the photoacoustic image and the ultrasound image. For example, the image synthesis section 27 performs image synthesis by superimposing the photoacoustic image and the ultrasound image. A synthesized image is displayed on an image display section 14, such as a display. Image synthesis may not be performed, and the photoacoustic image and the ultrasound image may be displayed in parallel on the image display section 14, or the photoacoustic image and the ultrasound image may be switched.

The control section 28 controls the respective units in the ultrasound unit 12. The control section 28 performs control for instructing the solid-state laser device 100 to emit light. For example, the control section 28 sends a trigger signal to the solid-state laser device 100. If the trigger signal is received, control section (not shown) in the solid-state laser device 100 turns on the flash lamp 112, and then, switches the Q value of the resonator from the low Q state to the high Q state with the Q switch 116 to emit pulse laser light. The control section 28 sends a sampling trigger signal to the AD conversion section 22 in conformity with the timing at which the subject is irradiated with light emitted from the solid-state laser device 100 and controls a sampling start timing of the photoacoustic wave.

The control section 28 sends an ultrasonic transmission trigger signal to instruct the transmission control circuit 29 to transmit the ultrasonic wave at the time of the generation of the ultrasound image. If the ultrasonic transmission trigger signal is received, the transmission control circuit 29 allows the ultrasonic wave to be transmitted from the probe 11. The control section 28 sends the sampling trigger signal to the AD conversion section 22 according to the ultrasonic transmission timing, and starts the sampling of the reflected ultrasonic wave.

In the above description, although a case where the probe 11 detects both the photoacoustic wave and the reflected ultrasonic wave in the photoacoustic measurement device 10 has been described, the probe for use in generating the ultrasound image and the probe for use in generating the photoacoustic image may not necessarily be the same. The photoacoustic wave and the reflected ultrasonic wave may be respectively detected by different probes. Furthermore, in the foregoing embodiments, although an example where the solid-state laser device constitutes a part of the photoacoustic measurement device has been described, the solid-state laser device of the invention may be used for a device different from the photoacoustic measurement device.

Although the invention has been described based on the preferred embodiment, the solid-state laser device and the photoacoustic measurement device of the invention are not limited to the foregoing embodiments, and various and corrections and alterations may be carried out from the configurations of the foregoing embodiments and may fall within the scope of the invention.

EXPLANATION OF REFERENCES

100: solid-state laser device
111: laser rod
112: flash lamp
113: laser chamber
114, 115: mirror
116: Q switch
117: prism
118: housing
119: shielding lid
120: thin film portion
121: insulating block
123: insulating member
124: thin film
141, 142: duct
131, 132: hole portion
133: O ring attachment portion
134: O ring
151: frame body
155: diffusion material
156: glass material
157, 158: storage hole
230: cooling equipment
231, 232: piping
10: photoacoustic measurement device
11: probe
12: ultrasound unit
14: image display section
21: reception circuit
22: AD conversion section
23: reception memory
24: data separation section
25: photoacoustic image generation section
26: ultrasound image generation section
27: image synthesis section
28: control section
29: transmission control circuit

What is claimed is:
1. A solid-state laser device comprising:
a laser rod;
an excitation lamp which emits excitation light to the laser rod;
a laser chamber which includes a frame body having an internal space storing the laser rod and the excitation lamp and transmits light emitted from the excitation lamp to the laser rod inside the frame body, a first portion of the frame body storing the excitation lamp having a first hole portion having a diameter greater than the outer diameter of the excitation lamp and a second portion of the frame body storing the laser rod having a second hole portion into which the laser rod is inserted;

a pair of mirrors provided on the optical path of a light beam emitted from the laser rod;

a housing to which the laser chamber and the pair of mirrors are directly attached; and a shielding portion which shields the second portion of the frame body of the laser chamber attached to the housing, the pair of mirrors, and the optical path of the light beam emitted from the laser rod from the outside, wherein the first portion of the frame body of the laser chamber further has an O ring attachment portion in which an O ring having an outer diameter greater than the diameter of the first hole portion is attached to an end portion in a longitudinal direction, the excitation lamp is able to be removed from and inserted into the laser chamber intermediated by the first hole portion, and the thickness of at least a part of a region of the shielding portion covering the optical path of the light beam emitted from the second hole portion is smaller than the thickness of other portions of the shielding portion on the outside in the longitudinal direction from the first portion of the frame body of the laser chamber.

2. The solid-state laser device according to claim 1, wherein the shielding portion includes a plate-shaped lid portion which has an opening wider than the laser chamber and an insulating member which closes the opening of the plate-shaped lid portion and has a duct, through which the light beam emitted from the laser rod passes, and the laser chamber is attached to the housing intermediated by the insulating member.

3. The solid-state laser device according to claim 2, wherein the first portion of the frame body of the laser chamber is exposed from the insulating member.

4. The solid-state laser device according to claim 2, wherein the duct is a through hole formed in the insulating member, and the thickness of a partition wall of the insulating member which separates the outside on the first portion side of the frame body from the through hole is smaller than the thickness of the plate-shaped lid portion.

5. The solid-state laser device according to claim 3, wherein the duct is a through hole formed in the insulating member, and the thickness of a partition wall of the insulating member which separates the outside on the first portion side of the frame body from the through hole is smaller than the thickness of the plate-shaped lid portion.

6. The solid-state laser device according to claim 4, wherein the duct has a cylindrical shape, the diameter of the cylindrical duct is greater than the diameter of the light beam emitted from the laser rod, and the central axis of the light beam passing through the cylindrical duct is deviated in the direction of the first portion of the frame body of the laser chamber from the central axis of the cylindrical duct.

7. The solid-state laser device according to claim 2, wherein the duct is a groove which is formed in the insulating member and has an opening in the direction of the first portion of the frame body of the laser chamber, the shielding portion further has a film which covers the opening of the duct, and the thickness of the film is smaller than the thickness of the plate-shaped lid portion.

8. The solid-state laser device according to claim 3, wherein the duct is a groove which is formed in the insulating member and has an opening in the direction of the first portion of the frame body of the laser chamber, the shielding portion further has a film which covers the opening of the duct, and the thickness of the film is smaller than the thickness of the plate-shaped lid portion.

9. The solid-state laser device according to claim 1, wherein the shielding portion is constituted of a plate-shaped lid portion, and of the plate-shaped lid portion, the thickness of at least a part of a region covering the optical path of the light beam emitted from the second hole portion is smaller than the thickness of other portions of the plate-shaped lid portion on the outside in the longitudinal direction from the first portion of the frame body of the laser chamber.

10. The solid-state laser device according to claim 2, wherein the frame body is formed of a metal material.

11. The solid-state laser device according to claim 3, wherein the frame body is formed of a metal material.

12. The solid-state laser device according to claim 4, wherein the frame body is formed of a metal material.

13. The solid-state laser device according to claim 5, wherein the frame body is formed of a metal material.

14. The solid-state laser device according to claim 6, wherein the frame body is formed of a metal material.

15. The solid-state laser device according to claim 7, wherein the frame body is formed of a metal material.

16. The solid-state laser device according to claim 8, wherein the frame body is formed of a metal material.

17. The solid-state laser device according to claim 10, further comprising:

an insulating block which is detachably attached to the first portion of the frame body of the laser chamber intermediated by an O ring.

18. The solid-state laser device according to claim 1, wherein the length in the longitudinal direction of the first portion of the frame body is longer than the length in the longitudinal direction of the second portion of the frame body.

19. The solid-state laser device according to claim 1, wherein the laser chamber further has, in the space, a glass material which has a first storage hole having an inner diameter greater than the outer diameter of the excitation lamp and storing the excitation lamp, and a second storage hole having an inner diameter greater than the outer diameter of the laser rod and storing the laser rod therein.

20. A photoacoustic measurement device comprising:
the solid-state laser device according to claim 1;
a photoacoustic wave detection section for detecting a photoacoustic wave generated in a subject after the subject has been irradiated with laser light emitted from the solid-state laser device reflected from; and
a signal processing section for carrying out signal processing based on the detected photoacoustic wave.

\* \* \* \* \*